(12) United States Patent
Suenaga et al.

(10) Patent No.: US 12,410,389 B2
(45) Date of Patent: Sep. 9, 2025

(54) CELL CULTURING METHOD AND DEVICE

(71) Applicant: TOYO SEIKAN GROUP HOLDINGS, LTD., Tokyo (JP)

(72) Inventors: Ryo Suenaga, Yokohama (JP); Maki Mitsuishi, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 660 days.

(21) Appl. No.: 16/615,017

(22) PCT Filed: Jun. 12, 2018

(86) PCT No.: PCT/JP2018/022344
§ 371 (c)(1),
(2) Date: Nov. 19, 2019

(87) PCT Pub. No.: WO2018/230544
PCT Pub. Date: Dec. 20, 2018

(65) Prior Publication Data
US 2020/0199508 A1      Jun. 25, 2020

(30) Foreign Application Priority Data
Jun. 15, 2017   (JP) ................. 2017-118066

(51) Int. Cl.
  *C12M 1/00*       (2006.01)
  *C12M 1/34*       (2006.01)
  *C12N 1/20*       (2006.01)
(52) U.S. Cl.
  CPC ............ *C12M 23/14* (2013.01); *C12M 41/36* (2013.01); *C12M 41/40* (2013.01); *C12N 1/20* (2013.01)

(58) Field of Classification Search
  CPC ...... C12M 23/14; C12M 41/36; C12M 41/40; C12N 1/20
  (Continued)

(56) References Cited

U.S. PATENT DOCUMENTS 5,316,905 A * 5/1994 Mori ..................... C12M 29/26
                                                                435/297.1
2010/0055764 A1 * 3/2010 Martin .................. C12M 23/14
                                                                435/243
(Continued)

FOREIGN PATENT DOCUMENTS

EP       3 495 467 A1     6/2019
JP       2005-295904 A    10/2005
(Continued)

OTHER PUBLICATIONS

Lindstrom et al., Single-Cell Culture in Microwells, Chapter 5 in Single-Cell Analysis Methods and Protocols, Methods in Molecular Biology 853, Springer Protocols, Humana Press, (2012), pp. 41-52.*
(Continued)

*Primary Examiner* — Jennifer M. H. Tichy
(74) *Attorney, Agent, or Firm* — Sughrue Mion, PLLC

(57) ABSTRACT

A cell culturing method using a cell culturing bag (1) in which a plurality of recess portions are formed, including: a bag body (2) configured from an upper film (21) and a lower film (22) which seal a peripheral portion; and a port (3) mounted on the bag body (2), wherein the cell culturing bag (1) is placed on a placement surface (5a) of a stand (5), and while a culture medium (S) is being injected or discharged from the port (3), a pressing member (6) having a bottom surface (6a) substantially parallel to the placement surface (5a) is used to press the upper film (21) from above.

4 Claims, 11 Drawing Sheets

(58) Field of Classification Search
USPC .......................................................... 435/383
See application file for complete search history.

(56) References Cited

U.S. PATENT DOCUMENTS

| | | | |
|---|---|---|---|
| 2016/0095279 A1* | 4/2016 | Brown | C12M 23/46 47/66.7 |
| 2016/0208210 A1* | 7/2016 | Kim | C12M 41/40 |
| 2016/0208219 A1 | 7/2016 | Suenaga et al. | |
| 2017/0362559 A1 | 12/2017 | Hata et al. | |
| 2019/0031994 A1 | 1/2019 | Tanaka et al. | |
| 2019/0300835 A1 | 10/2019 | Suenaga et al. | |
| 2020/0318057 A1* | 10/2020 | Hata | C12N 5/0662 |

FOREIGN PATENT DOCUMENTS

| | | |
|---|---|---|
| JP | 2009-11260 A | 1/2009 |
| JP | 2012-44872 A | 3/2012 |
| JP | 2016-39796 A | 3/2016 |
| JP | 2016-86774 A | 5/2016 |
| WO | 2014/208004 A1 | 12/2014 |
| WO | 2016/121292 A1 | 8/2016 |
| WO | 2016/208526 A1 | 12/2016 |
| WO | 2017/170335 A1 | 10/2017 |

OTHER PUBLICATIONS

Extended European Search Report dated Feb. 3, 2021 in corresponding Application No. 18817921.2.
International Preliminary Report on Patentability with a Translation of Written Opinion in International Application No. PCT/JP2018/022344, issued on Dec. 17, 2019.
International Search Report in International Application No. PCT/JP2018/022344, issued on Aug. 28, 2018.

* cited by examiner

CELL CULTURING METHOD AND DEVICE

CROSS REFERENCE TO RELATED APPLICATIONS

This application is a National Stage of International Application No. PCT/JP2018/022344 filed Jun. 12, 2018, claiming priority based on Japanese Patent Application No. 2017-118066 filed Jun. 15, 2017.

TECHNICAL FIELD

The present invention relates to a cell culturing method and device, more specifically, a cell culturing method and device using a cell culturing bag.

BACKGROUND ART

In recent years, there is demand for efficiently culturing and inducing differentiation of cells (including tissues, microorganisms, viruses and the like) in large quantities under an artificial environment in fields such as production of a pharmaceutical, gene therapy, regenerative medicine and immunotherapy.

In such cell culture, a closed-system cell culturing bag is used in several cases in order to avoid a risk of contamination. The cell culturing comprises a bag body configured from a plastic film which seals a peripheral portion and a port mounted on the bag body, for example.

Cell culture using the cell culturing bag requires avoidance of a bias of a cell concentration in the cell culturing bag to maintain the cell concentration in a proper range because, if the cell concentration in a culture medium increases with multiplication of cells, growth of the cells is inhibited by exhaustion of a medium component required for the multiplication, accumulation of metabolites of the cells per se, or the like, whereby efficiency of multiplication of the cells is reduced, and on the other hand, if the cell concentration in the culture medium is excessively low, efficiency multiplication and induction differentiation of the cells is reduced.

In particular, in spheroid culture using the cell culturing bag having a plurality of recess portions, the cells are inseminated to be uniform in the number of the cells so that a spheroid (cell aggregate) having an appropriate size may be formed in each recess portion. Then, one spheroid per recess portion is required to be maintained until completion of culture so that a size of the spheroid in each recess portion may be uniformized.

Patent Document 1 describes a cell culturing bag in which transfer of cells in the cell culturing bag is suppressed by providing a plurality of recess portions in a bottom surface of a bag body.

RELATED ART DOCUMENTS

Patent Documents

Patent Document 1: JP-A-2009-11260

DISCLOSURE OF THE INVENTION

Problems to be Solved by the Invention

Cell culture ordinarily requires a period of several days to several weeks. In cell culture using a cell culturing bag, during a culture period, while maintaining a closed system, a culture medium is replaced, when necessary. In replacing the culture medium, while leaving cells in the cell culturing bag, an old culture medium in the cell culturing bag is discharged from a port through a liquid feed tube connected to the port, and then a new culture medium is injected into the cell culturing bag from the port.

Incidentally, while replacing the culture medium, undulation such as wrinkles or distortion occurs on an upper film of the cell culturing bag in several cases. In particular, as shown in FIG. 9A, a cell culturing bag 10 in which an upper film 21 is formed into a swelling shape is superior to a flat pouch-shaped container prepared only by stacking two plastic films and sealing a peripheral portion in that, even if an inside of the container is filled with a culture medium, the peripheral portions of a lower film 22 are unlikely lifted up and deformed. However, the undulation easily occurs in the upper film 21.

If discharge of a culture medium S is continued while the undulation occurs in the upper film 21 of the cell culturing bag 10, and a thickness of the culture medium S in a cell culturing bag 1 is non-uniformized, as shown in FIG. 9B, the upper film 21 is partly brought into contact with the lower film 22 in a thin region Sa of the culture medium S faster than in a thick region Sb of the culture medium S. As a result, a dividing part D which divides the culture medium S in the cell culturing bag 1 is formed in several cases.

When the dividing part D is formed in the cell culturing bag 10, as shown in FIG. 9C, even if the culture medium S is sucked from a port 3, only the culture medium S on a front side further than the dividing part D is discharged. On the other hand, a residual culture medium S1 on a back side further than the dividing part D is not discharged, and is left in the cell culturing bag 1. As a result, replacement efficiency of the culture medium S is reduced, and efficiency of culture and induction differentiation of the cells is reduced.

While replacing the culture medium, when the dividing part D as shown in FIG. 9C is formed, if the cell culturing bag 10 is inclined to be lowered on a side of the port 3, division of the culture medium S in the cell culturing bag 10 is dissolved, whereby the residual culture medium S1 which is left therein can be discharged. However, if the cell culturing bag 1 is inclined, the cells are liable to be discharged from the port 3 together with the culture medium S, and also in the cell culturing bag 1 having the plurality of recess portions 4 in the lower film 22 shown in FIG. 11, even the cells are liable to flow out from the recess portion 4 together with the culture medium in the recess portion 4. Therefore, it is not preferable to incline the cell culturing bag 10 while replacing the culture medium.

Further, when plane culture (two-dimensional culture) of the cells is performed on the lower film 22, if the upper film 21 is partly brought into contact with the lower film 22 by the undulation of the upper film 21, the cells adhering to the lower film 22 in a part in the contact are peeled, resulting in being discharged from the port 1 together with the culture medium S in several cases. Moreover, even when the cells peeled therefrom are not discharged from the port 1, the cells move in the cell culturing bag 1 to cause a bias of a cell concentration in several cases.

When the thickness of the culture medium S is non-uniform by the undulation of the upper film 21, as shown in FIGS. 10A and 10B, a flow speed of the culture medium S when replacing the culture medium locally increases in the thin region Sa of the culture medium S in the cell culturing bag 1 than in the thick region Sb of the culture medium S therein. As a result, in a part in which the flow speed of the culture medium increases, the cells easily move.

For example, when the plane culture of the cells is performed on the lower film 22, even if the upper film 21 is not brought into contact with the lower film 22, in the part in which the flow speed of the culture medium increases, the cells adhering to the lower film 22 are peeled in several cases. As a result, when replacing the culture medium, the cells peeled therefrom move together with the culture medium, resulting in being discharged from the port 3 in several cases.

For example, as shown in FIG. 11, also when spheroid culture is performed in the cell culturing bag 1 having the plurality of recess portions 4 in the lower film 22, if the flow speed of the culture medium S locally increases upon replacing the culture medium, a spheroid cell C having been deposited in the recess portion 4 is liable to move together with the culture medium S, resulting in being discharged from the port 3, and also the spheroid cell C is transferred to any other recess portion 4, whereby the cell concentration in each recess portion 4 is non-uniformized in several cases. In particular, if a plurality of spheroids Center in one recess portion 4, the plurality of spheroids C are eventually formed into a spheroid C' in one large aggregate, whereby the spheroid C' becomes excessively large, and therefore efficiency of culture and induction differentiation is reduced.

The present invention has been made in view of the above-described circumstances, and an objective of the present invention is to provide a cell culturing method and device, wherein when performing cell culture using a cell culturing bag, the efficiency of culture and induction differentiation of the cells can be improved by improving the replacement efficiency of culture media while preventing cell movement when replacing the culture medium.

Means for Solving the Problems

A cell culturing method according to the present invention, using a cell culturing bag comprising: a bag body configured from an upper film and a lower film which seal a peripheral portion; and a port mounted on the bag body, wherein the cell culturing bag is placed on a placement surface of a stand, and while a culture medium is being injected or discharged from the port, a pressing member having a bottom surface substantially parallel to the placement surface is used to press the upper film from above.

Moreover, a cell culturing device according to the present invention, using a cell culturing bag comprising: a bag body configured from an upper film and a lower film which seal a peripheral portion and a port mounted on the bag body, comprising: a stand having a placement surface on which the cell culturing bag is placed; and a pressing member having a bottom surface substantially parallel to the placement surface, wherein, while the culture medium is being injected or discharged from the port, the bottom surface of the pressing member presses the upper film from above.

According to the cell culturing method and device of the present invention, in cell culture using the cell culturing bag, while the culture medium is being injected or discharged from the port, the pressing member having the bottom surface substantially parallel to the placement surface is used to press the upper film, whereby occurrence of undulation of the upper film is suppressed. As a result, while the culture medium is being injected or discharged, the upper film is kept parallel to the placement surface of the stand, whereby a thickness of the culture medium is uniformized.

Thus, while the culture medium is being discharged or injected, occurrence of division of the cell culturing bag by the undulation of the upper film is suppressed, and a residual culture medium which is left in the cell culturing bag is reduced, and therefore replacement efficiency of the culture media is improved.

Moreover, while the culture medium is being discharged or injected, the thickness of the culture medium is uniform, and therefore occurrence of flow speed unevenness by thickness unevenness of the culture medium is suppressed. As a result, occurrence of a locally large flow speed of the culture medium is suppressed, and therefore cell movement is prevented.

For example, when plane culture of cells is performed on the lower film, upon replacing the culture medium, cell peeling and movement by partial contact of the upper film or a local increase in the flow speed are prevented.

Moreover, for example, also when spheroid culture is performed in the cell culturing bag having a plurality of recess portions in the lower film, upon replacing the culture medium, movement of a spheroid cell in the recess portion, particularly, transfer to any other recess portion 4 by the local increase in the flow speed is prevented.

Advantageous Effects of the Invention

According to a cell culturing method and device of the present invention, when performing cell culture using a cell culturing bag, efficiency of culture and induction differentiation of the cells can be improved by improving replacement efficiency of culture media while preventing cell movement when replacing the culture medium.

BRIEF DESCRIPTION OF THE DRAWINGS

FIGS. 1A-1C show an explanatory diagram showing an outline of a cell culturing bag used in an embodiment of the present invention, in which FIG. 1A shows a plan view, FIG. 1B shows a side view, and FIG. 1C shows a bottom view.

FIGS. 2A and 2B show a schematic cross-sectional view of a cell culturing device according to a first embodiment of the present invention, in which FIG. 2A shows a state in which a pressing member rises, and FIG. 2B shows a state in which the pressing member falls.

FIGS. 4A and 4B show schematic cross-sectional-view views showing a cell culturing method according to an embodiment of the present invention, in which FIG. 4A shows a state before discharging a culture medium, and FIG. 4B shows a state after discharging the culture medium.

FIGS. 7A and 7B show schematic cross-sectional views showing a cell culturing method according to a third embodiment of the present invention, in which FIG. 7A shows a large discharge flow rate when a liquid thickness is large, and FIG. 7B shows a small discharge flow rate when the liquid thickness is small.

FIGS. 8A and 8B are schematic cross-sectional views showing a cell culturing method according to an embodiment of the present invention, in which FIG. 8A shows a state before discharging a culture medium, and FIG. 8B shows a state after discharging the culture medium.

FIGS. 9A-9C show schematic cross-sectional views of a cell culturing bag, in which FIG. 9A shows a state in which undulation occurs in an upper film, FIG. 9B shows a state in which a culture medium is divided when discharging the culture medium, and FIG. 9C shows a state in which the culture medium is left when discharging the culture medium.

MODE FOR CARRYING OUT THE INVENTION

Figure 1C:
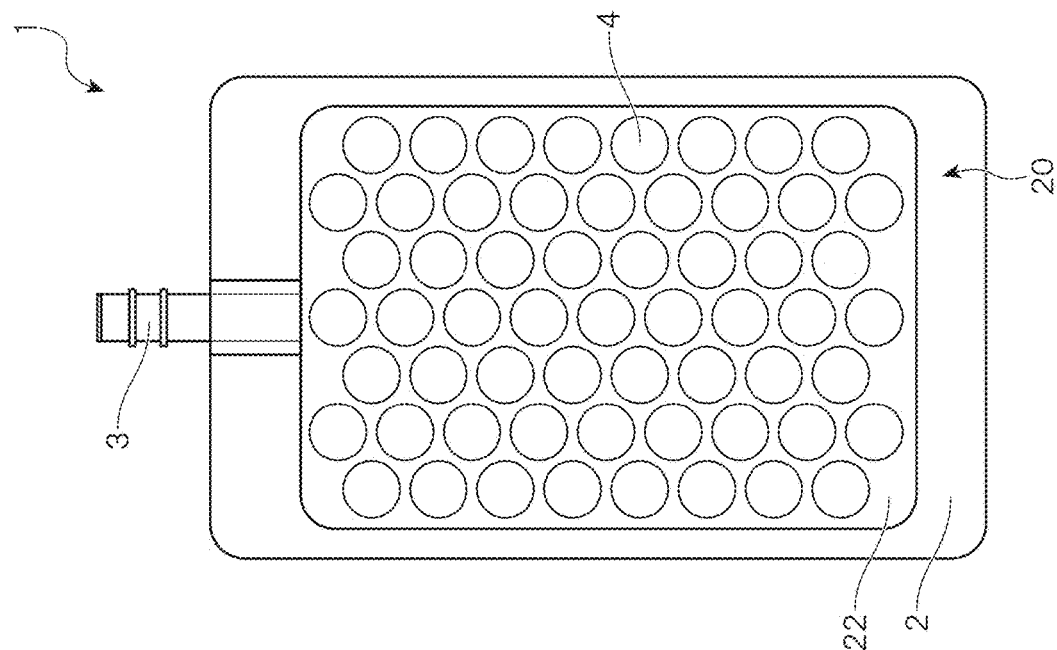

Hereinafter, an embodiment of the present invention will be described with reference to drawings.
(Cell Culturing Bag)

First, a cell culturing bag used in first to third embodiments will be described with reference to FIGS. 1A and 1B prior to description of a cell culturing device according to an embodiment. A cell culturing bag 1 shown in FIG. 1A to FIG. 1C comprises: a bag body 2 configured from an upper film 21 and a lower film 22 which are stacked to heat seal a peripheral portion 20; and a port 3 mounted on the bag body 2. A size of the bag body 2 is not particularly limited, and is preferably adjusted to 50 to 500 mm in length and 50 to 500 mm in width, for example.

Figure 1B:
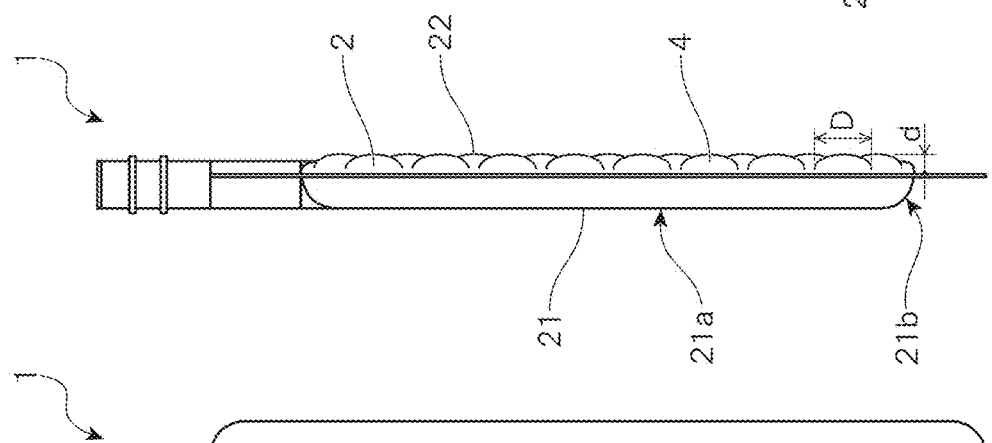
Figure 1A:
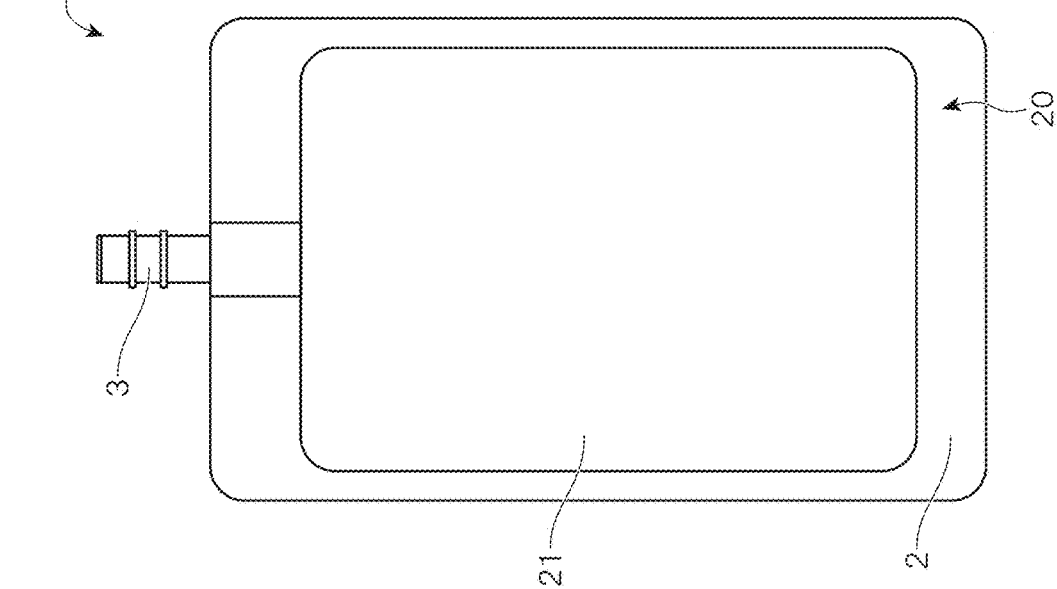

In each drawing including FIGS. 1A-1C, illustration of a flow path such as a tube connected to the port 3 and illustration of a closing means such as a pinch or a valve which closes the flow path are omitted.

As shown in FIG. 1C, a plurality of recess portions 4 each serving as a cell culture portion are formed in the lower film 22. In the recess portion 4, an opening diameter (diameter) D is preferably 0.3 to 10 mm, and a depth d is preferably 0.1 mm or more, in order to suppress cell transfer in the bag body 2 to retain the cells under culture in one recess portion 4. The recess portions 4 may also be formed into the same opening diameter in all the recess portions 4, or may include two or more kinds of recess portions having a different opening diameter. For example, the lower film 22 may be divided into a plurality of regions, and the opening diameter of the recess portion 4 may be differed for each region. In that case, upon injecting cells to be cultured into the bag body 2 together with the culture medium, the opening diameter of the recess portion 4 is preferably increased on a side of the peripheral portion so that the same degree of the number of cells may be precipitated and entered in all the recess portions 4.

As shown in FIG. 1B, the recess portion 4 in the cell culturing bag 1 is formed into a spherical crown shape in order to facilitate gathering of the cells in a bottom portion of the recess portion 4. The shape of the recess portion 4 is not limited thereto. A ratio d/D of depth d to a diameter D of the recess portion 4 is preferably adjusted to 0.05 to 1 in order to facilitate gathering of the cells in the bottom portion of the recess portion 4.

The recess portions 4 are preferably aligned in a staggered shape as shown in FIG. 1C so that an occupied area of the recess portion 4 in the lower film 22 may be as large as possible, but the recess portion 4 may be aligned in a lattice shape, when necessary.

As shown in FIG. 1B, the upper film 21 has a swelling shape which is swollen into a plateau shape configured from: a substantially flat top surface part 21a covering an upper part of a whole of the plurality of recess portions 4; and a rising part 21b formed on a circumference of the top surface part 21a. Thus, even if the bag body 2 is filled with the culture medium, deformation in which the peripheral portion of the lower film 22 is lifted up is suppressed in comparison with a flat pouch-shaped container prepared only by stacking two plastic films and sealing a peripheral portion.

The upper film 21 and the lower film 22 which form the bag body 2 are formed of a plastic film having gas transmission. The gas transmission of the plastic film is preferably 5,000 mL/(m$^2$·day·atm) or more in an oxygen transmission rate measured at a test temperature of 37° C. in accordance with determination of gas-transmission rate in JIS K 7126.

Specific examples of a material to be used in the plastic film which forms the bag body 2 include a thermoplastic resin of polyethylene, polypropylene, an ethylene-vinyl acetate copolymer, polyester, a silicone-based elastomer, a polystyrene-based elastomer, a tetrafluoroethylene-hexafluoropropylene copolymer (FEP) or the like. The materials may be used in a single layer or by laminating the same kind or different kinds of materials, but if heat sealability upon heat sealing the peripheral portion is taken into consideration, the material preferably has a layer which functions as a sealant layer.

A thickness of the plastic film which forms the bag body 2 is preferably 30 to 200 μm at which the film has moderate shape retainability so that the upper film 21 may keep the swelling shape while having flexibility, and the lower film 22 may keep a shape of the recess portion 4.

The port 3 is formed of a tubular member through which the medium, the cells or the like can flow, and can be formed of the thermoplastic resin of polyethylene, polypropylene, vinyl chloride, a polystyrene-based elastomer, FEP or the like, for example.

First Embodiment

Figure 2A:
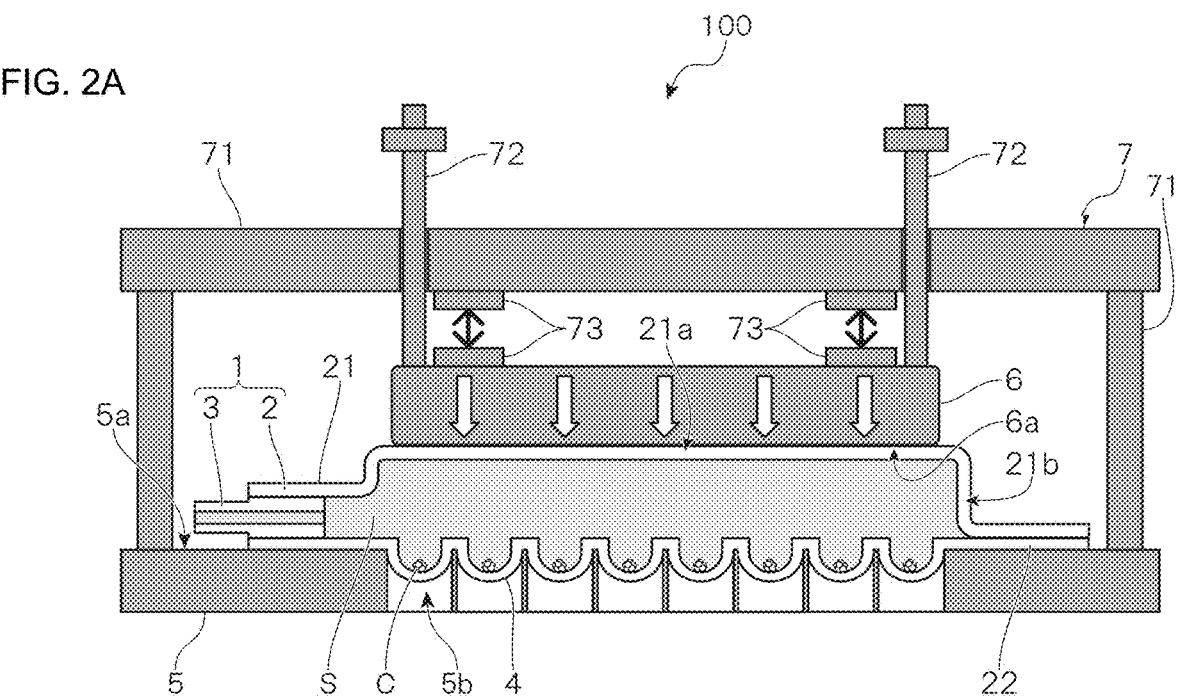
Figure 2B:
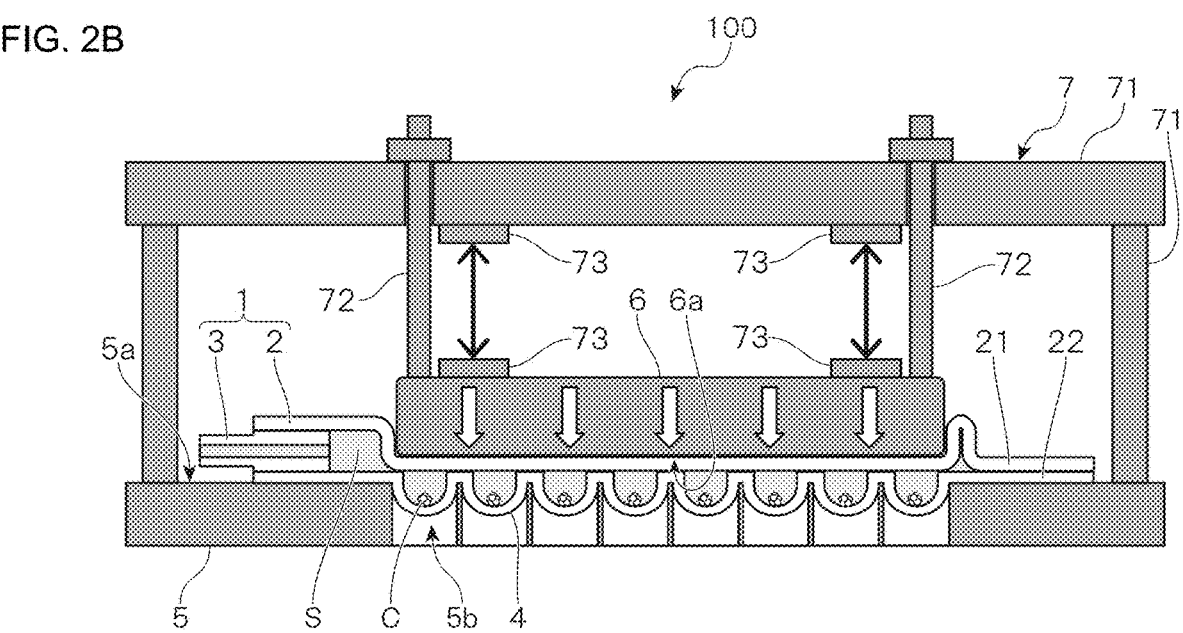

Next, a cell culturing method and device according to the embodiment of the present invention will be described with reference to FIGS. 2A and 2B. FIGS. 2A 2B are schematic cross-sectional views of a cell culturing device 100 according to a first embodiment, in which FIG. 2A shows a state in which a pressing member rises, and FIG. 2B shows a state in which the pressing member falls.

The cell culturing device 100 in the present embodiment comprises: a stand 5 on which the cell culturing bag 1 is placed; a pressing member 6 having a bottom surface 6a which presses a portion of the top surface part 21a of the upper film 21; and a support mechanism 7 which supports the pressing member 6. Further, the cell culturing device 100 in the present embodiment is provided with an injection and discharge means (not shown) such as a pump connected to the port 3.

The stand 5 has a placement surface 5a on which the cell culturing bag 1 is horizontally placed. In the placement surface 5a, an opening 5b is formed as a shape for receiving each of the plurality of recess portions 4 formed in the lower film 22 of the cell culturing bag 1. Thus, the placement surface 5a supports the lower film 22 in non-contact with the recess portion 4, and therefore flattening and deformation of the recess portion 4 are avoided, whereby outflow of the cells in the recess portion 4 is prevented, and further gas transmission from the lower film 22 is improved.

The shape for receiving each of the plurality of recess portions 4 is not limited to the opening, and may be the recess portion or a wire net shape, for example.

The pressing member 6 is a 10 mm-thick plate-shaped member having a substantially rectangular planar shape according to the top surface part 21a of the cell culturing bag 1, and has the flat bottom surface 6a substantially parallel to the placement surface 5a of the stand 5.

For example, the pressing member 6 may be formed of a synthetic resin such as polycarbonate, or formed of glass. Moreover, the pressing member 6 preferably partly or wholly has transparency so as to be able to confirm progress of cell culture, a state of the cells, or the like.

The support mechanism 7 is configured from: a frame 71 provided on the stand 5; guide pins 72 which are extended upward from four corners of an upper surface of the pressing member 6 to penetrate the frame 71 so as to be able to vertically move: and biasing means 73 which bias the pressing member 6 downward. The biasing means 73 are configured from permanent magnets 73 which are arranged on the upper surface of the pressing member 6, and the frame 71 with the same pole sides facing each other. According to repulsive force applied between the permanent magnets 73, the pressing member 6 vertically moves according to a height of the upper film 21 while pressing the upper film 21 from above.

Thus, upon injecting the culture medium, while the pressing member 6 presses the upper film 21, the culture medium S is injected from the port 3 by the injection and discharge means connected to the port 3. Also upon discharging the culture medium, while the pressing member 6 presses the upper film 21, the culture medium S is discharged from the port 3 by the injection and discharge means.

The biasing means 73 is not limited to the permanent magnet. Moreover, the biasing means 73 may be omitted, and according to self-weight of the pressing member 6, the pressing member 6 may vertically move according to the height of the upper film 21.

While injecting or discharging the culture medium from the port 3, the bottom surface 6a of the pressing member 6 presses the top surface part 21a of the upper film 21, whereby occurrence of undulation by wrinkles or distortion is suppressed in the top surface part 21a of the upper film 21. Then, according to the support mechanism 7, the bottom surface 6a of the pressing member 6 is kept parallel to the placement surface 5a of the stand 5. Thus, while replacing the culture medium, the top surface part 21a of the upper film 21 is kept parallel to the placement surface 5a of the stand 5, whereby a thickness of the culture medium S in the cell culturing bag 1 is uniformized.

Thus, when replacing the culture medium, occurrence of flow speed unevenness by thickness unevenness of the culture medium is suppressed, whereby a local increase in the flow speed of the culture medium is suppressed, and therefore outflow of the cells from the recess portion 4 is prevented.

Moreover, when discharging the culture medium, the top surface part 21a of the upper film 21 is to be brought into contact with a circumference of the recess portion 4 of the lower film 22 substantially simultaneously in the whole area, and therefore an inside of the cell culturing bag 1 is not divided. Therefore, the residual culture medium which is left in the cell culturing bag 1 is reduced, and therefore the replacement efficiency of the culture media is improved.

Thus, when replacing the culture medium, while preventing outflow of the cell C from the recess portion 4 to maintain a uniform cell concentration, the residual culture medium is reduced, whereby replacement efficiency of the culture medium S is improved, and therefore efficiency of culture and induction differentiation of the cells can be improved.

When discharging the culture medium, the pressing member 6 descends, whereby the top surface part 21a of the upper film 21 closes each of the plurality of recess portions 4. Thus, the cell C is each confined in each recess portion 4, and therefore when discharging the culture medium, the cell C in the recess portion 4 is prevented from being discharged together with the culture medium S.

The cell C is confined in each recess portion 4, and therefore the cell C does not flow out from the recess portion 4, even if the port 3 is closed with a valve (not shown) or the like to remove the cell culturing device 100 or the culturing bag 1 from a CO2 incubator, whereby such operation is performed as inclination or application of vibration or shock, for example, conveying to a different cell treating division or the like. Thus, while a cell spheroid C formed one by one in each recess portion 4 is separated from the cell spheroid C in any other recess portion 4, the cell spheroid C in each recess portion 4 can be transferred at one time.

Figure 3A:
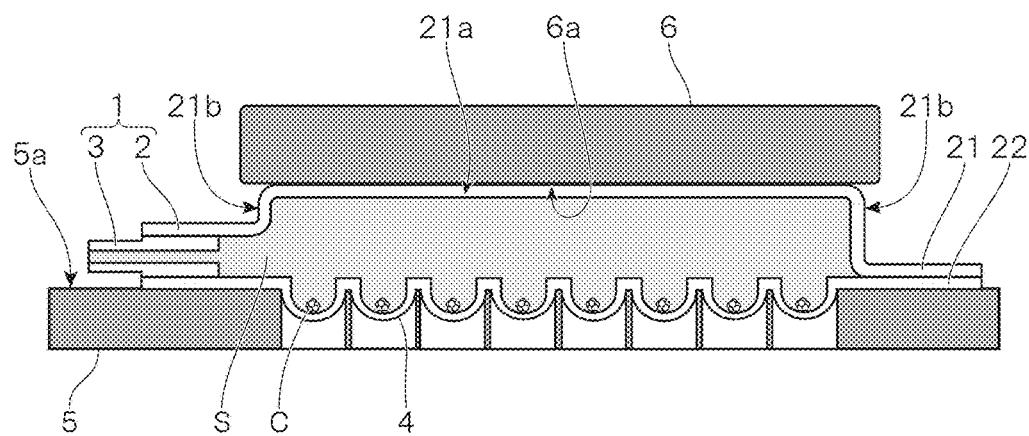
FIG. 3A shows a schematic cross-sectional view showing a magnitude relationship between a top surface part of a cell culturing bag and a bottom surface of a pressing member.
Figure 3B:
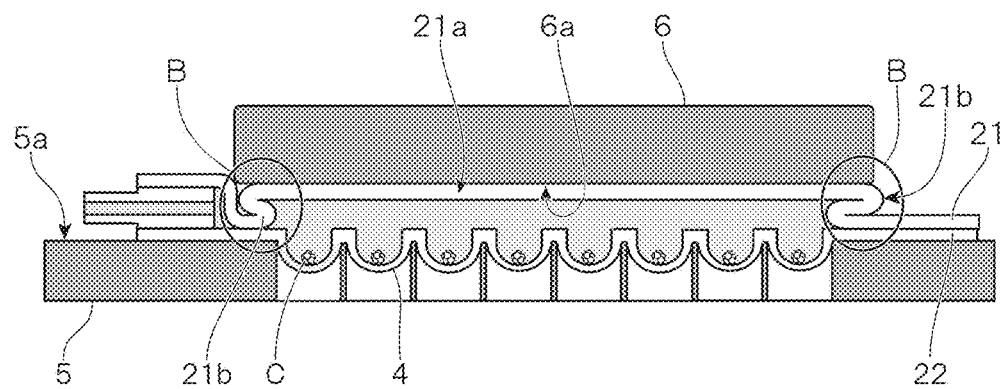
FIG. 3B shows a schematic cross-sectional view showing an aspect in which the pressing member interposes the cell culturing bag therebetween.

Incidentally, as shown in FIG. 3A, when the bottom surface 6a of the pressing member 6 is wider than the top surface part 21a of the upper film 21 of the cell culturing bag 1, the bottom surface 6a of the pressing member 6 descended causes stamping on the rising part 21b of the upper film 21. As shown by a circle B in FIG. 3B, if the rising part 21b of the upper film 21 is interposed between the bottom surface 6a of the pressing member 6 and the placement surface 5a of the stand 5, the top surface part 21a of the upper film 21 is unable to be brought into contact with the lower film 22, whereby each of the recess portions 4 becomes hard to be closed by the upper film 21.

Figure 4A:
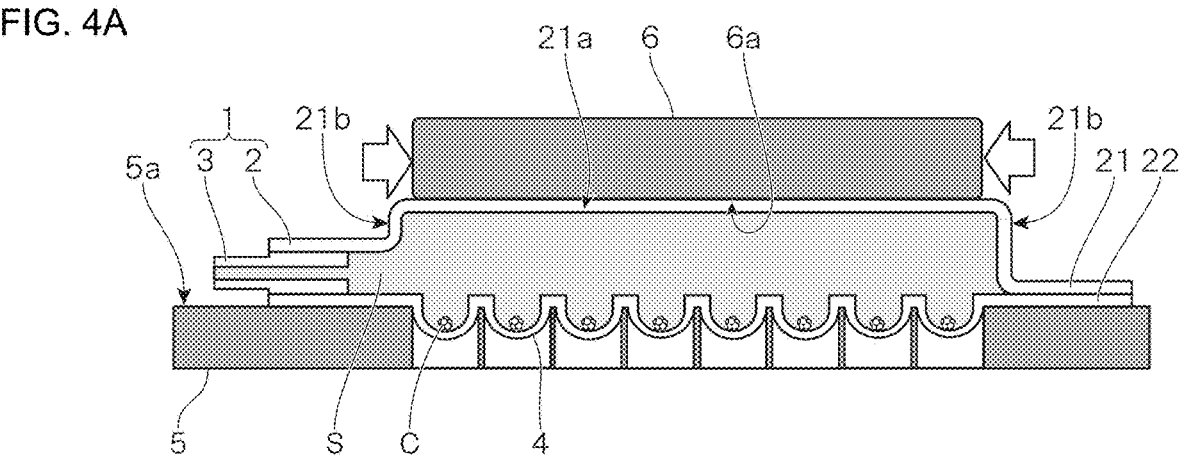
Figure 4B:
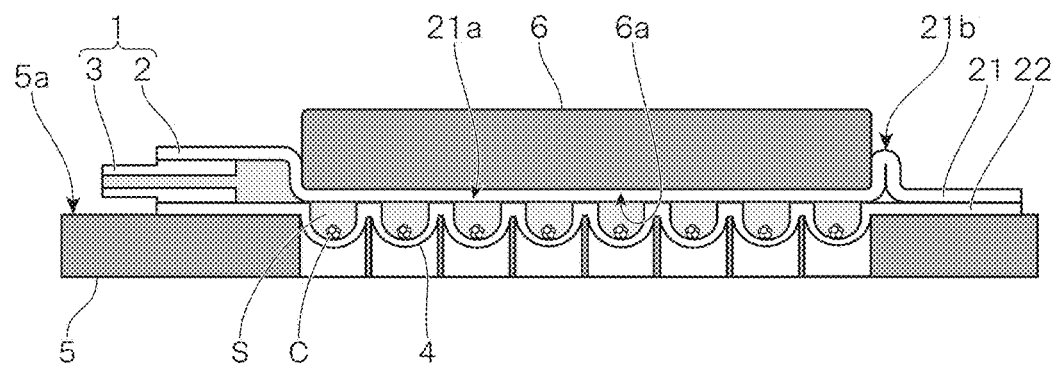

Accordingly, in the present embodiment, as shown in FIG. 4A, the pressing member 6 is dimensioned so that the bottom surface 6a of the pressing member 6 may be arranged on an inner side than the rising part 21b of the upper film 21. Thus, as shown in FIG. 4B, when discharging the culture medium, the pressing member 6 descends, the bottom surface 6a of the pressing member 6 is brought into contact with the top surface part 21a in the range on the inner side than the rising part 21b to press the upper film 21, whereby each of the plurality of recess portions 4 can be closed by the top surface part 21a of the upper film 21, in which the bottom surface 6a causes no stamping on the rising part 21b.

When closing the recess portion 4 by the upper film 21, outflow of the cells from the recess portion 4 only needs to be prevented, and the recess portion 4 need not be necessarily tightly closed. Moreover, all the recess portions 4 are preferably closed by the top surface part 21a of the upper film 21, but all of the recess portion 4 need not be necessarily closed.

In order to avoid stamping of the rising part 21b by the pressing member 6 descended, the pressing member 6 only needs to have a size and shape in which the bottom surface 6a is brought into contact with the top surface part 21a only in the range on the inner side than the rising part 21b, and an upper part of the pressing member 6 may be projected on an outer side than the rising part 21b.

Second Embodiment

Next, a cell culturing method and device according to a second embodiment will be described with reference to FIGS. 5A and 5B. A structure of the cell culturing device in the present embodiment is the same as in the first embodiment shown in FIGS. 1A-1C except for a shape of a pressing member 60. Illustration of the support mechanism 7 shown in FIGS. 1A-1C are omitted in FIGS. 5A and 5B.

Figure 5A:
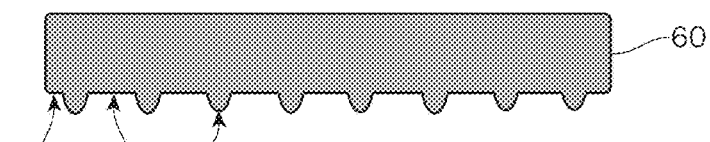
FIG. 5A shows a schematic cross-sectional view of a pressing member in a cell culturing device according to a second embodiment of the present invention.

As shown in FIG. 5A, a bottom surface 60a of the pressing member 60 has: plane portions 61 in positions corresponding to peripheral edges of the plurality of recess portions 4; and projection portions 62 projecting from the plane portions 61 in positions corresponding to the plurality of recess portions 4.

In order for the cell C in the recess portion 4 to avoid being damaged, a height of the projection portion 62 to the plane portion 61 is preferably smaller than a depth of the recess portion 4 of the lower film 22. Moreover, the projection portions 62 are preferably provided in positions corresponding to all the recess portions 4, but need not be necessarily provided in the positions corresponding to all the recess portions 4.

Figure 5B:
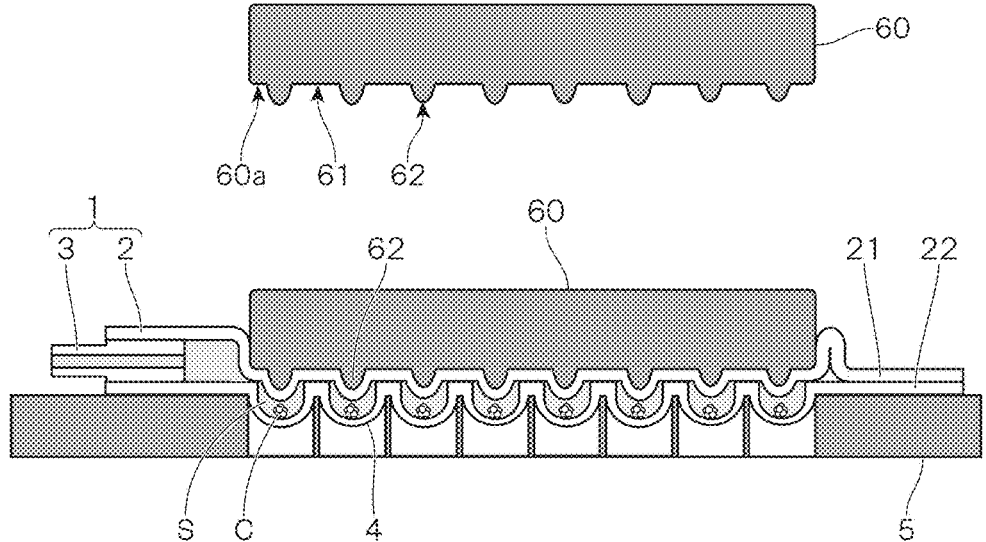
FIG. 5B shows a schematic cross-sectional view showing the cell culturing device according to the second embodiment of the present invention.

As shown in FIG. 5B, when the culture medium is discharged, and the pressing member 60 descends, and each of the plurality of recess portions 4 is closed by the top surface part 21a of the upper film 21, the upper film 21 is inserted into each recess portion 4 of the lower film 22 by the projection portion 62 of the bottom surface 60a of the pressing member 60. As a result, the culture medium S which remains in each recess portion 4 is reduced by a volume of the projection portion 62 in comparison with the first embodiment. Thus, replacement efficiency of the culture medium S is improved, whereby efficiency of culture and induction differentiation of the cells can be further improved.

Third Embodiment

Next, a cell culturing method and device according to a third embodiment will be described with reference to FIG. 6 and FIGS. 7A and 7B. Illustration of the support mechanism 7 shown in FIGS. 1A-1C are omitted in FIG. 6.

A structure of the cell culturing device of the present embodiment is the same as in the first embodiment except for a flow rate control means (not shown) which controls a flow rate of the culture medium S passing through the port 3 when injecting and discharging the culture medium S from the port 3. As the flow rate control means, for example, a pump such as a peristaltic pump or a syringe pump connected to the port 3 through a tube can feed a liquid with high precision at a low rate, and therefore such a pump is preferable.

As described in the first embodiment, when replacing the culture medium, the pressing member 6 is used to press the upper film 21 of the cell culturing bag 1, thereby uniformizing the thickness of the culture medium S, whereby flow speed unevenness of the culture medium in the bag body 2 is reduced, and outflow of the cells from the recess portion 4 is suppressed.

However, if the flow rate of the culture medium S passing through the port 3 is extremely large, even if the pressing member 6 is used, the cell C flows out from the recess portion 4 in several cases. On the other hand, if the flow rate of the culture medium S passing through the port 3 is extremely small, though outflow of the cell C from the recess portion 4 can be prevented, a long period of time is required for replacing the culture medium.

Figure 6:
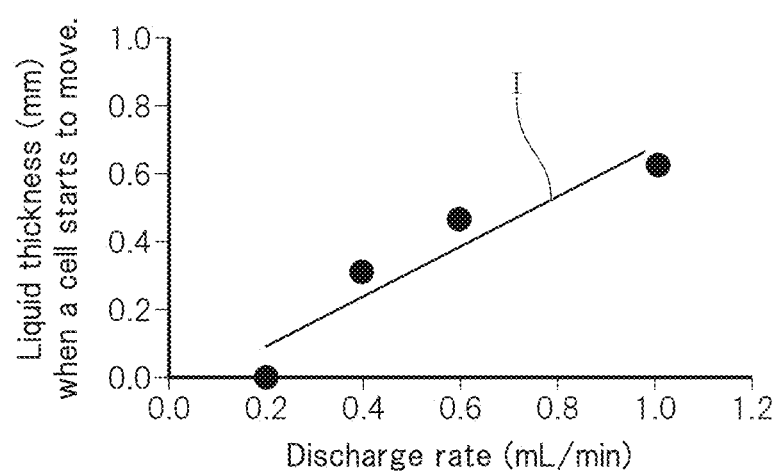
FIG. 6 shows a graph showing a relationship between a discharge rate of a culture medium and a liquid thickness when a cell starts to move.

Here, FIG. 6 shows a graph showing a relationship between the flow rate (discharge rate (mL/min)) of the culture medium S passing through the port 3 when discharging the culture medium and a liquid thickness (mm) when the cell starts to move. This liquid thickness represents a distance between the upper film 21 and an edge portion of the recess portion 4 of the lower film 22. A length obtained by adding thicknesses of the upper and lower films 21 and 22 to the liquid thickness substantially corresponds to a height from the placement surface 5a of the stand 5 to the bottom surface 6a of the pressing member 6.

As shown by a straight line I in the graph, as the liquid thickness of the culture medium S is smaller, the cell C starts to move at a smaller flow rate. The reason is that, when the flow rate passing through the port 3 is constant, as the liquid thickness of the culture medium S is larger, a flow path in the bag body 2 becomes wider to reduce the flow speed of the culture medium S, and therefore the cell C becomes hard to flow, and on the other hand, as the liquid thickness is smaller, the flow path in the bag body 2 becomes narrower to increase the flow speed of the culture medium S, and therefore the cell C becomes easy to flow.

Figure 7A:
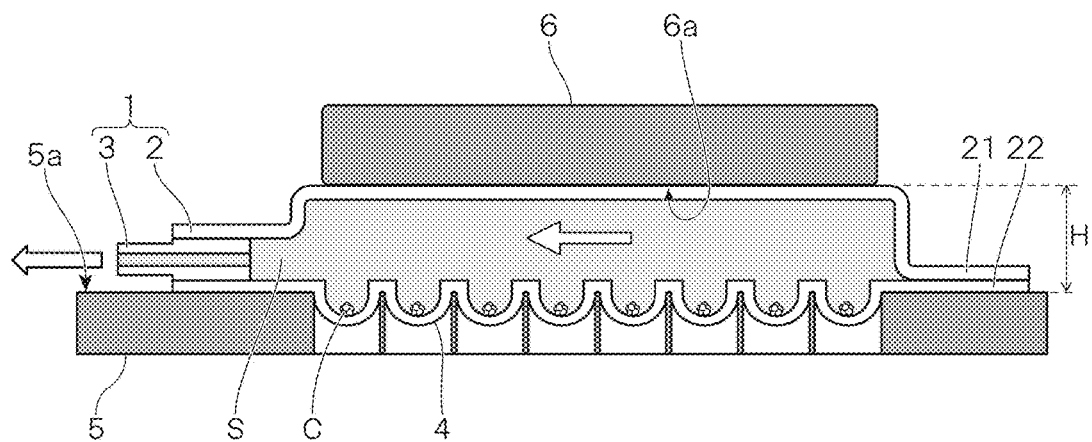
Figure 7B:
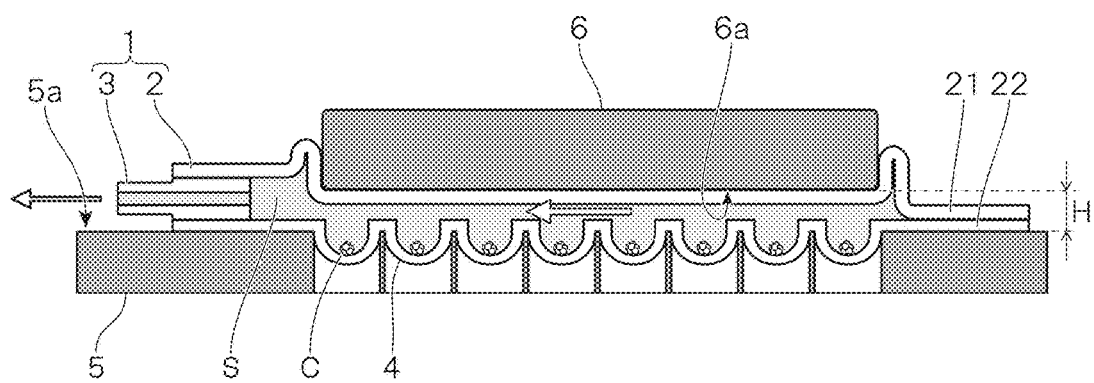

Based on the above-described finding, in the present embodiment, the flow rate control means controls the flow rate in such a manner that, as shown in FIG. 7A, as a height H from the placement surface 5a of the stand 5 to the bottom surface 6a of the pressing member 6 is higher, the flow rate of the culture medium S passing through the port 3 is larger, and as shown in FIG. 7B, as the height H from the placement surface 5a of the stand 5 to the bottom surface 6a of the pressing member 6 is lower, the flow rate of the culture medium S passing from the port 3 is smaller. More specifically, upon discharging the culture medium S, accordingly as the liquid thickness becomes smaller, the flow rate of the culture medium S to be discharged from the port 3 is adjusted to be smaller, and upon injecting the culture medium S, accordingly as the liquid thickness becomes larger, the flow rate of the culture medium S to be injected from the port 3 is adjusted to be larger.

In the flow rate control, the flow rate may be changed stepwise, or may be changed continuously. Moreover, specific numerical values of the flow rate to the liquid thickness are different depending on a shape of the bag body 2, a kind of the cell C, a shape of the recess portion 4, or the like, and therefore should be determined experimentally.

Such flow rate control allows shortening of a time required for replacing the culture medium while suppressing outflow of the cell C from the recess portion 4.

In the present embodiment, the flow rate control means is not limited to the pump serving also as the injection and discharge means connected to the port 3, and various means which enable flow rate adjustment can be adopted.

For example, the flow rate can also be controlled by changing a cross-sectional area of the flow path connected to the port 3. Specifically, a variable valve or a throttling mechanism should be provided in the flow path. In this case, the cross-sectional area of the flow path is preferably changed while the culture medium is being sucked or delivered by the pump.

The flow rate can also be controlled by inserting an obstacle such as a mesh or a filter into the flow path connected to the port 3.

The flow rate can also be controlled by adjusting a pressure difference between a pressure in a chamber of an incubator or the like in which the cell culturing device is housed, and an atmospheric pressure. Specifically, upon discharging the culture medium S, accordingly as the liquid thickness becomes smaller, the pressure in the chamber should be reduced to decrease the flow rate of the culture medium S to be discharged from the port 3. On the other hand, upon injecting the culture medium S, accordingly as the liquid thickness becomes larger, the pressure in the chamber should be raised to increase the flow rate of the culture medium S to be injected from the port 3. In this case, the injection and discharge means such as the pump may be connected to the port 3 or need not be connected thereto.

Fourth Embodiment

A cell culturing method and device according to a fourth embodiment will be described with reference to FIGS. 8A and 8B.

Figure 8A:
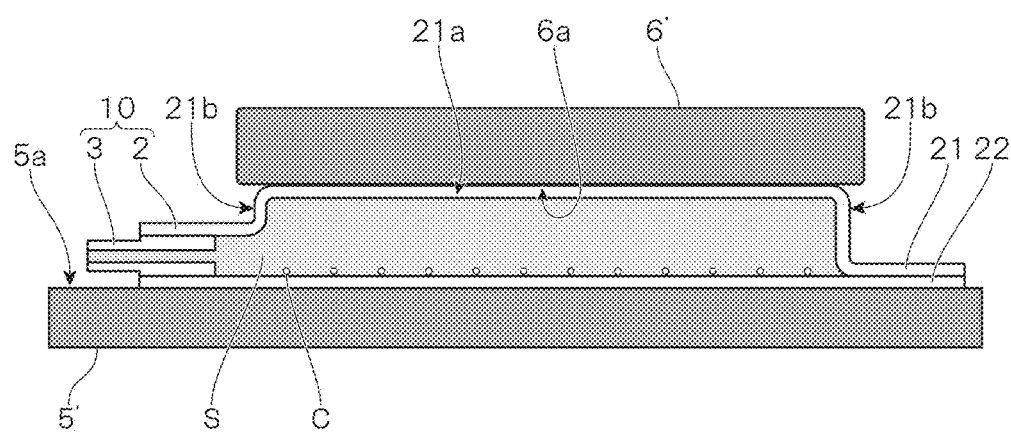
Figure 8B:
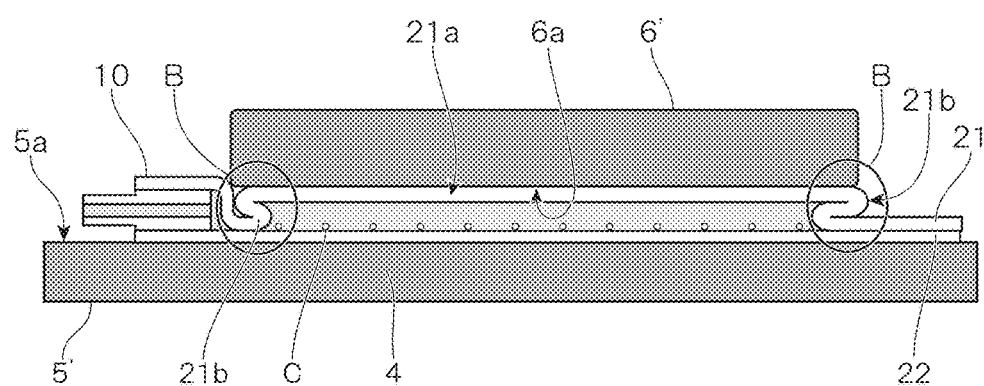
Figure 9A:
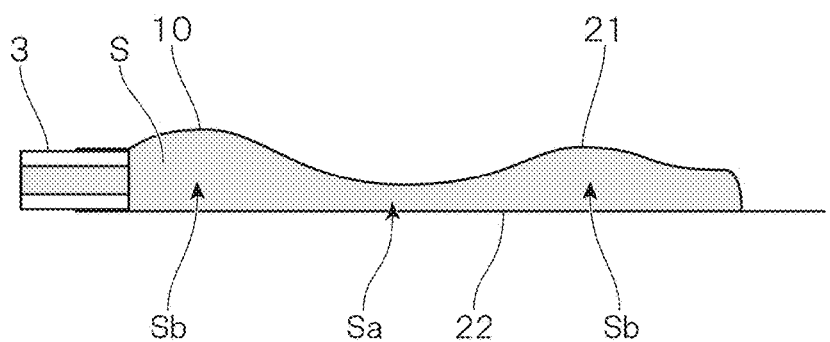
Figure 9B:
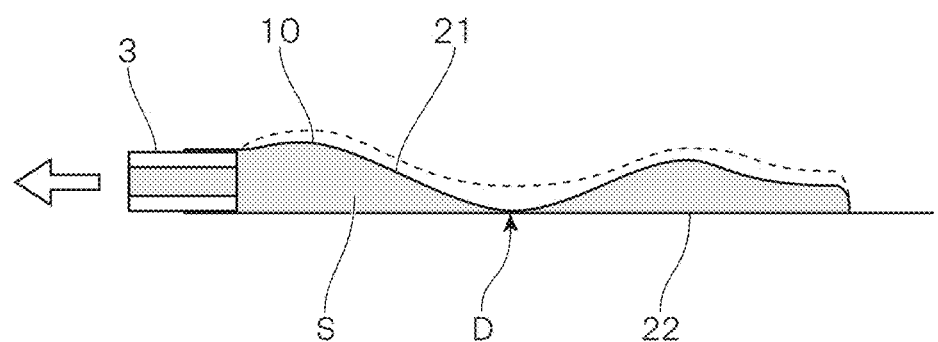
Figure 9C:
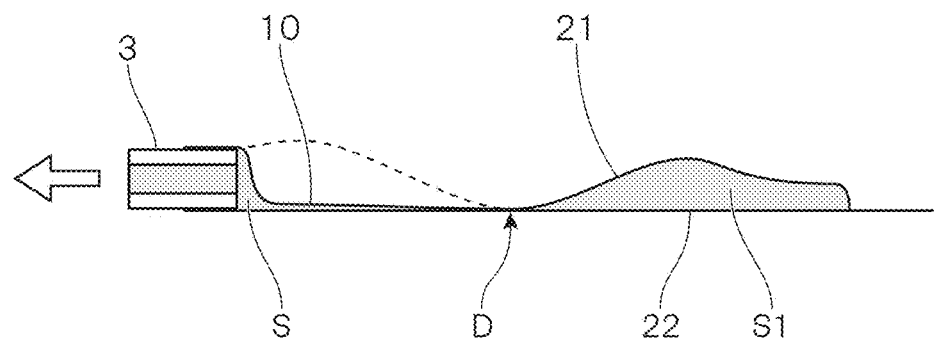
Figure 10A:
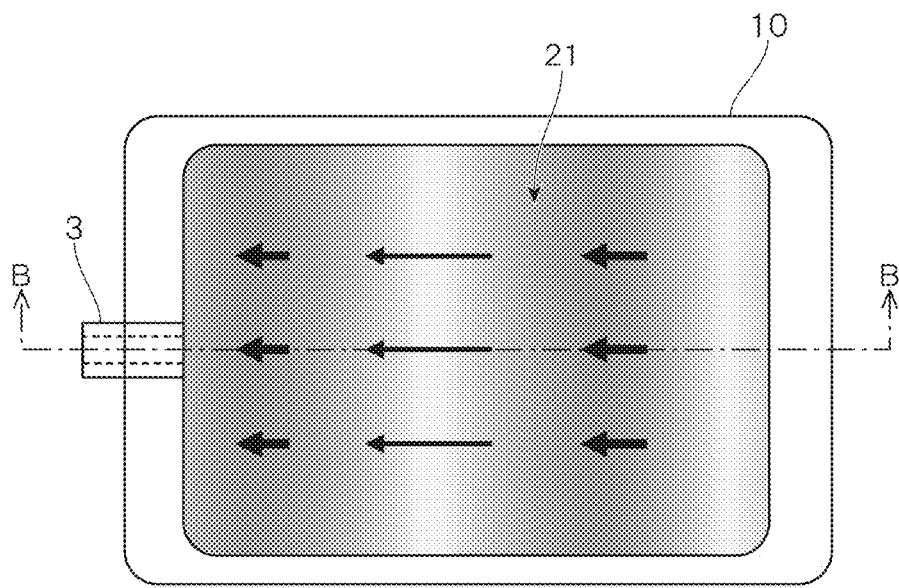
FIG. 10A shows a schematic plan view of a cell culturing bag.
Figure 10B:
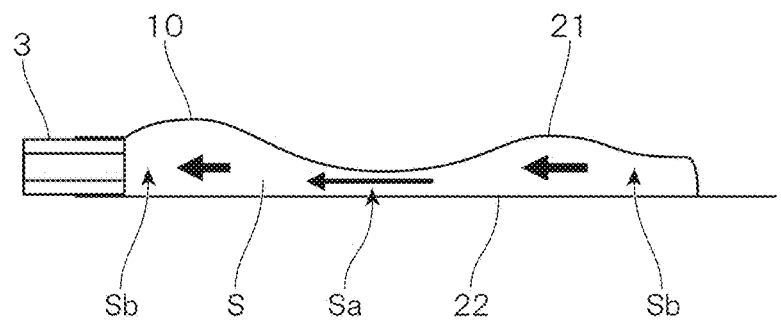
FIG. 10B shows a schematic cross-sectional view taken along a B-B line in FIG. 10A.
Figure 11:
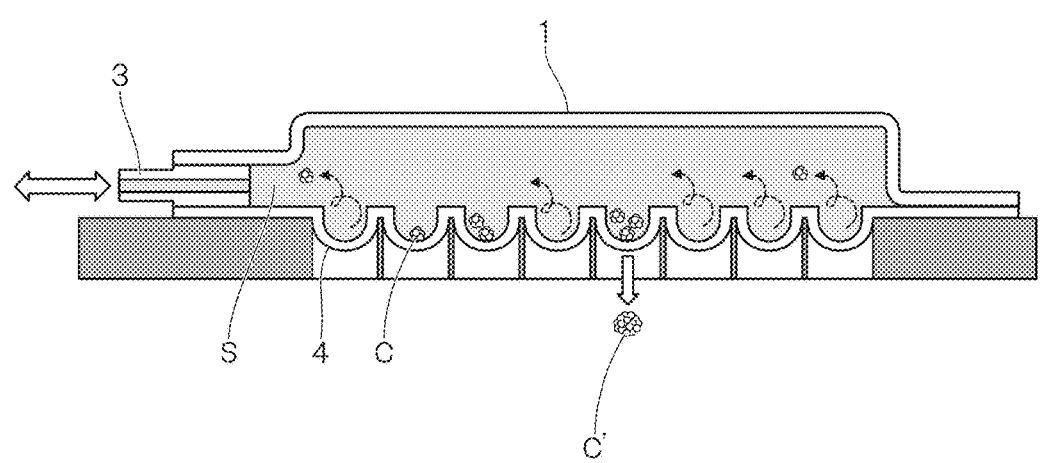
FIG. 11 shows a schematic cross-sectional view showing outflow of cells from recess portions in a cell culturing bag when replacing a culture medium.

In the first embodiment to the third embodiment described above, examples of the cell culturing method and device using the cell culturing bag 1 in which the plurality of recess portions 4 were formed in the lower film 22 were described, but the present invention can also be applied to a cell culturing method and device using a cell culturing bag 10 for plane culture in which no recess portions are formed in a lower film 22 as shown in FIGS. 8A and 8B.

The cell culturing bag 10 for plane culture used in the present embodiment is formed with the same dimensions and the same materials as the cell culturing bag 1 shown in FIGS. 1A-1C except that no recess portions are formed in the lower film 22.

The cell culturing device in the present embodiment has the same configuration as the cell culturing device 100 in the first embodiment shown in FIGS. 2A and 2B except for a stand 5' and a pressing member 6'.

As shown in FIG. 8A, a placement surface 5a of the stand 5' is flat, on which an opening for receiving the recess portion is not formed.

As shown in FIG. 8A, the pressing member 6' also has the flat bottom surface 6a, and the bottom surface 6a of the pressing member 6' has a larger dimension than the top surface part 21a of the upper film 21 of the cell culturing bag 10.

Therefore, if the pressing member 6' descends, as shown by a circle B in FIG. 8B, the bottom surface 6a of the pressing member 6' causes stamping on the rising part 21b of the upper film 21. As a result, the rising part 21b of the upper film 21 is interposed between the bottom surface 6a of the pressing member 6' and the placement surface 5a of the stand 5' to avoid contact between the upper film 21 and the lower film 22. Thus, when replacing the culture medium, the upper film 21 is prevented from being brought into contact with the cells adhering to the lower film 22, whereby peeling of the cells is prevented.

In the present embodiment, when the bottom surface 6a is narrower than the top surface part 21a, it is preferable that, for preventing peeling of the cells, the pressing member 6' stops descending so as to maintain a predetermined space between the upper film 21 and the lower film 22 to avoid contact between both the upper film 21 and the lower film 22.

As described above, the present invention is described by showing preferred embodiments, but the present invention is not limited to the embodiments described above, and various modifications can be obviously made within the scope of the present invention. For example, in the embodiments described above, the pressing member has the plate shape, but the shape of the pressing member is not limited thereto, and the pressing member may have projections and recesses on an upper surface, for example.

INDUSTRIAL APPLICABILITY

The present invention can be used as a technology on efficiently culturing various cells.

The entire contents of the documents described in the description concerning the present application and the description of the Japanese application serving as a basis of claiming the priority concerning the present application to the Paris Convention are incorporated by reference herein.

EXPLANATION OF NUMERICAL SYMBOLS

1, 10 Cell culturing bag
2 Bag body
20 Peripheral portion
21 Upper film
21a Top surface part
21b Rising part
22 Lower film
3 Port
4 Recess portion
5, 5' Stand
5a Placement surface
5b Opening
6, 6' pressing member
6a Bottom surface
60 pressing member
60a Bottom surface
61 Plane portion
62 Projection portion
7 Support mechanism
71 Frame
72 Guide pin
73 Permanent magnet
100 Cell culturing device
C Cell, spheroid
S Culture medium
S1 Residual culture medium
Sa Thin region of culture medium
Sb Thick region of culture medium

The invention claimed is:

1. A method for culturing cells, comprising:
   placing a cell culturing bag on a placement surface of a stand, wherein the cell culturing bag comprises a bag body configured from an upper film and a lower film which are sealed at a peripheral portion, and a port mounted on the bag body, wherein a plurality of recess portions each serving as a cell culture portion are formed in the lower film, wherein the upper film has a swelling shape which is swollen into a plateau shape configured from a flat top surface part; and rising parts standing from the lower film with predetermined height formed on a circumference of the top surface part, and wherein a plurality of openings or recess portions are formed on the placement surface of the stand in positions corresponding to the plurality of recess portions of the lower film as a shape for receiving each of the plurality of recess portions of the lower film;
   inseminating the cells into the bag body to provide a number of the cells in each recess portion so that a spheroid having an appropriate size is formed from the cells provided in each recess portion;
   discharging a culture medium from the port while simultaneously confining the cells or the spheroid in the plurality of recess portions; and
   the confining occurring by descending the pressing member to press the top surface part of the upper film from above, the pressing member having a bottom surface parallel to the placement surface, wherein the bottom surface of the pressing member is brought into contact with the top surface part of the upper film, and the pressing member descending until the upper film closes the plurality of recess portions.

2. The method for culturing cells according to claim 1, wherein the bottom surface of the pressing member has: plane portions in positions presenting over peripheral edges of the plurality of recess portions; and projection portions projected from the plane portions in positions presenting over the plurality of recess portions.

3. The method for culturing cells according to claim 1, wherein the culture medium is injected into the port and/or discharged from the port by an injection and discharge means connected to the port while the pressing member is being used to press the upper film.

4. The method for culturing cells according to claim 1, wherein, upon injecting or discharging the culture medium from the port, a flow rate is controlled in such a manner that, as a height of the upper film or the pressing member is lowered, a flow rate is adjusted to be slower.

\* \* \* \* \*